United States Patent [19]
Garcia

[11] Patent Number: 5,873,903
[45] Date of Patent: Feb. 23, 1999

[54] THERAPEUTIC SLEEVE FOR HUMAN LIMB

[76] Inventor: Andrea M. Garcia, 1441 Golden Harvest La., El Cajon, Calif. 92019

[21] Appl. No.: 803,092

[22] Filed: Feb. 20, 1997

[51] Int. Cl.$^6$ ........................................................ A61F 7/00
[52] U.S. Cl. .......................... 607/108; 607/112; 607/114; 2/912
[58] Field of Search ............................ 607/104, 108–112, 607/114; 126/204; 165/46; 2/912

[56]  References Cited

U.S. PATENT DOCUMENTS

| | | | |
|---|---|---|---|
| 4,800,867 | 1/1989 | Owens | 607/114 X |
| 5,456,704 | 10/1995 | Kilcullen | 607/111 |
| 5,575,013 | 11/1996 | Krack | 2/912 X |
| 5,591,221 | 1/1997 | Owens | 607/114 X |

*Primary Examiner*—Jeffrey R. Jastrzab
*Assistant Examiner*—Ryan Carter

[57]  ABSTRACT

A pair of stretchable therapeutic sleeve embodiments for slipping over a human limb such as a leg, an arm, or a foot. They each have a primary tubular member made of stretchable material and they are used in combination with a cool or hot pack for either cooling or heating a particular body member. One embodiment has a pocket wall secured to the inner surface of the primary tubular member for removably receiving the hot or cool pack. The other embodiment requires a hot or cool foot pack having a specific configuration that is positioned over a liner sleeve and inside the primary tubular member.

4 Claims, 2 Drawing Sheets

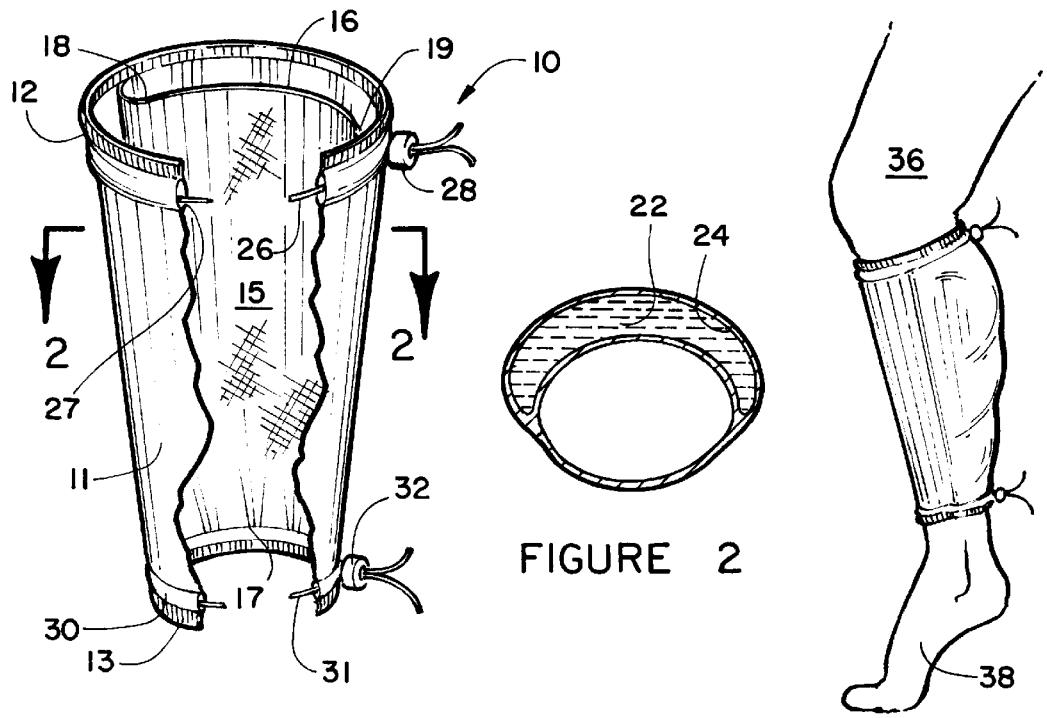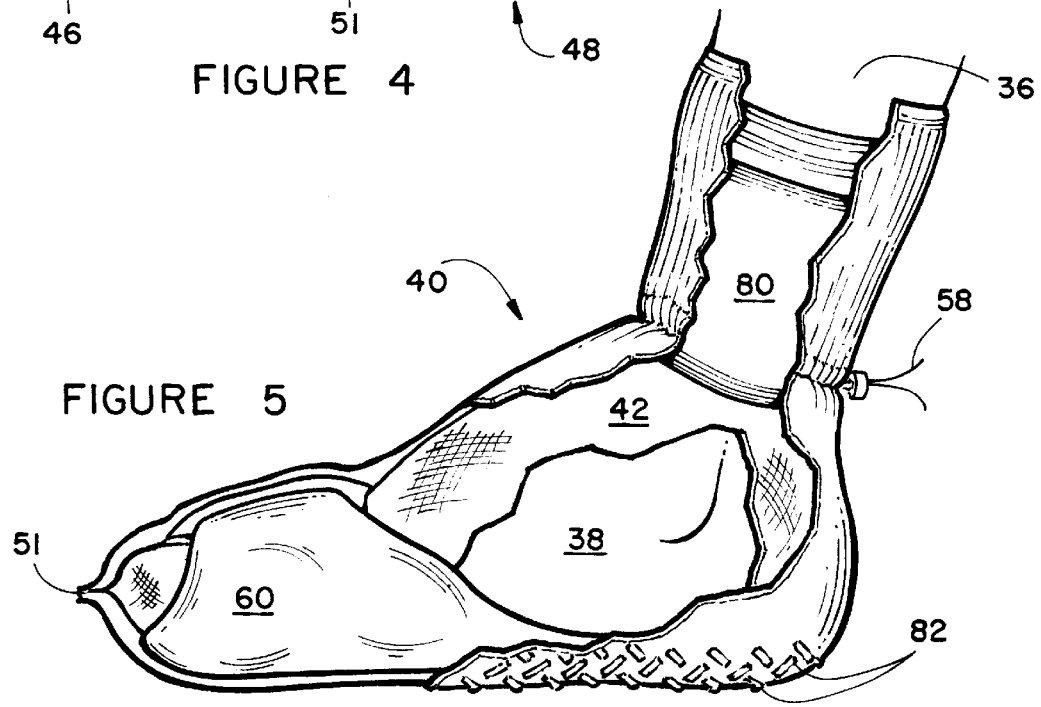

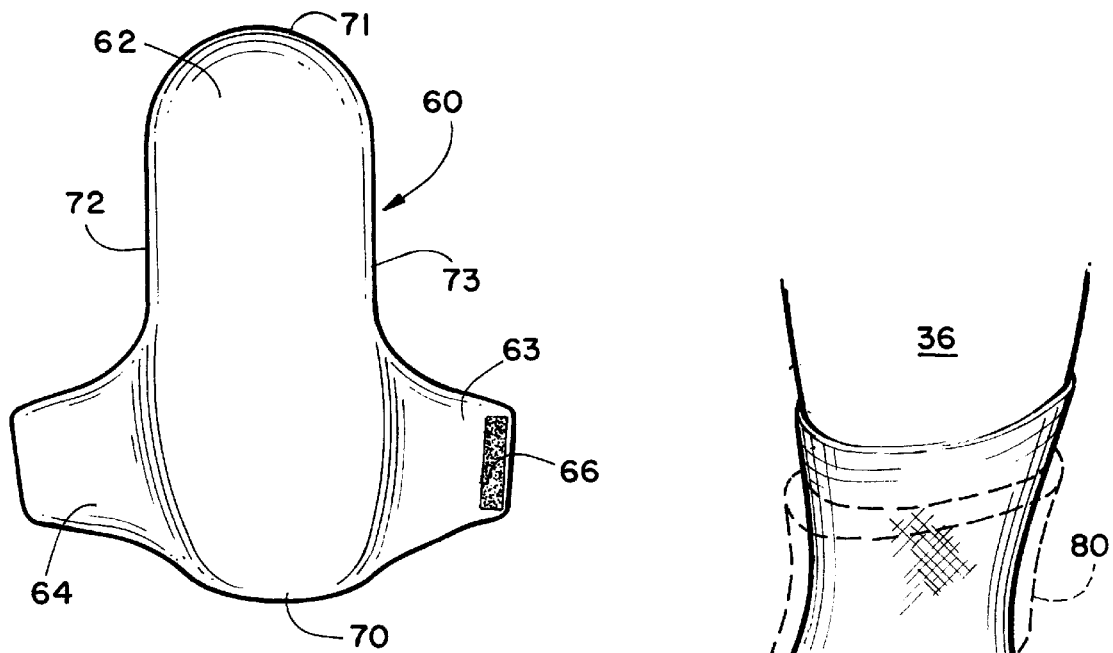
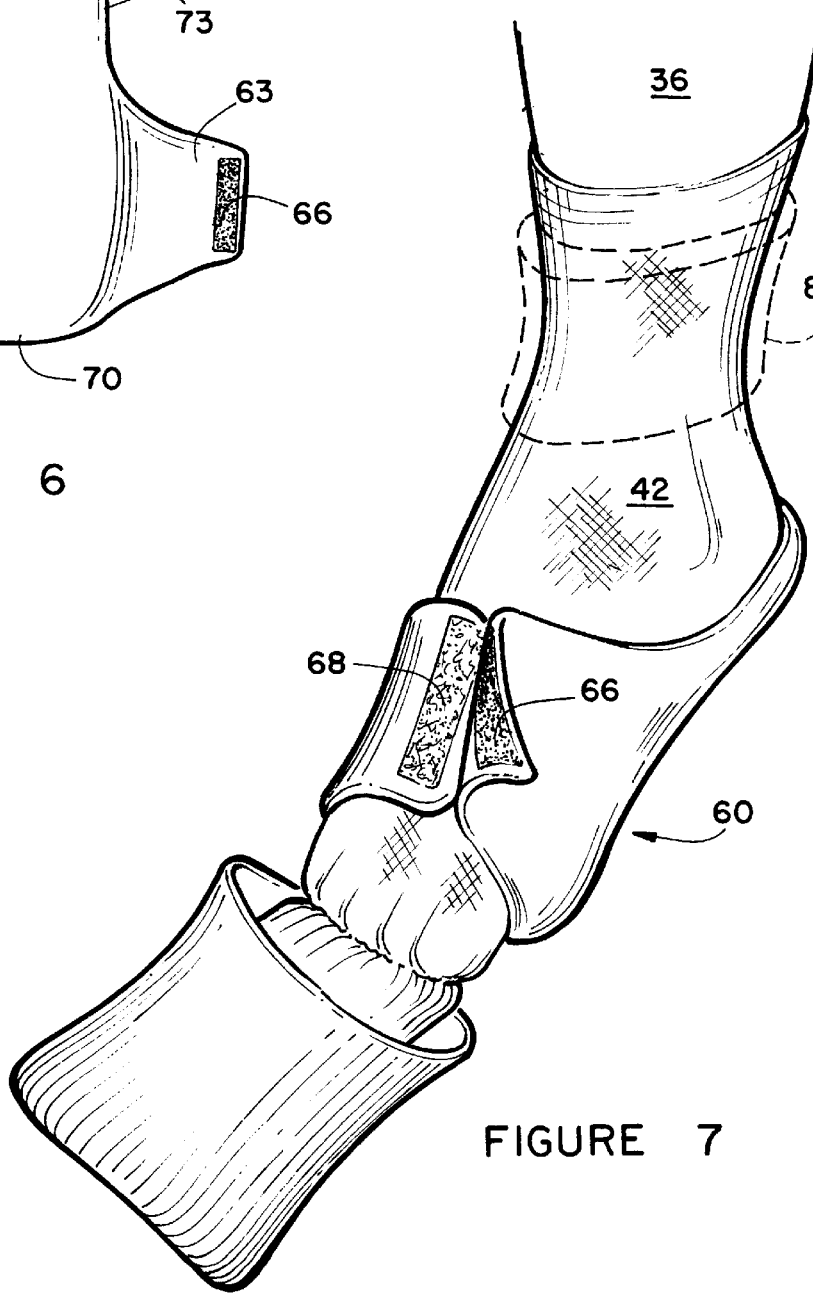
FIGURE 6
FIGURE 7 ns,873,903

THERAPEUTIC SLEEVE FOR HUMAN LIMB

BACKGROUND OF THE INVENTION

The present invention relates to therapeutic limb apparatus and more specifically to a stretchable therapeutic sleeve into which one or more hot or cool packs can be inserted for the treatment of or the prevention of injury of a limb.

Presently there exist many types of devices to be used with a cool or hot pack and then applied to an affected area of the human body.

Cold therapy is an established practice used in the medical profession to treat certain limb injuries. A few examples are sprained or strained arm or leg muscles or injuries to joints. Generally these types of injuries should be chilled to slow blood flow, which reduces swelling, pain and further damage.

Heat therapy is used, in other circumstances, to warm up or limber muscles by increasing blood flow.

The Hubbard U.S. Pat. No. 4,688,572 is directed to a medical/sports thermal pack. It has a first pocket and a second pocket connected together by a stretchable material. Therapeutic material holding bladders are insertable into the respective pockets.

The Tampa U.S. Pat. No. 4,628,932 is directed to a knee ice pack. It has a center compartment having a through opening intended to be aligned with the patella to preclude the patella from being subjected to the cooling effect of the ice.

The Natali U.S. Pat. No. 5,052,387 is directed to a cold pack for wrapping injured limbs and a method of making the same. It is made from two thermoplastic sheets of polyethylene material to provide a rectangular shape that has a small ice compartment defined at one of the rectangle's shorter sides. The opposite short side has a strip of adhesive covered with release paper.

The Turner U.S. Pat. No. 5,088,487 is directed to a flexible wrap for maintaining a thermal pack in heat transfer relation to the human anatomy. The thermal pack contains a quantity of liquid and filler particles which, when the liquid is frozen solid, produces a pliable thermal pack which conforms to contoured surfaces of the human body.

The Brunson et al U.S. Pat. No. 5,466,251 is directed to a therapeutic sleeve which can be secured to a patient's limb. It can be utilized with either a hot or cold pack.

SUMMARY OF THE INVENTION

The novel stretchable therapeutic sleeve embodiments have been designed for slipping over a human limb such as a leg, an arm or a foot. They each have a primary tubular member made of stretchable material such as lycra, and they are used with a hot or cool pack for heating or cooling a particular body member.

One embodiment has a pocket wall secured to the inner surface of the primary tubular member for receiving a hot or cool pack filled with a gel that would allow it to be foldable to conform to the appropriate body member. The pocket wall is preferably formed of a nylon/cotton material whose bottom edge and lateral side edges would be sewn to the inner surface of the primary tubular member. Upper and lower drawstring members would be threaded through their respective annular horizontal sleeves formed in the primary tubular member. In addition, there would be a horizontal elastic strip formed along the top and bottom edges of the primary tubular member.

The alternative embodiment stretchable therapeutic sleeve has a primary tubular member whose bottom end is stitched to the bottom end of a liner sleeve of stretchable material. Initially the liner sleeve is pulled onto the foot and lower leg of the person. Next a hot or cool foot pack is positioned under the bottom of the person's foot and its flaps or wings folded up over the top of the foot and secured to each other by hook and loop fasteners. The primary tubular member is then pulled onto the foot over top of the hot or cool foot pack until it reaches the ankle of the person. A second hot or cool pack is then folded around the person's lower leg/ankle area and the top end of the primary tubular member is pulled upwardly over the hot or cool pack. A drawstring may be tightened to secure the cool pack in its proper location.

Some of the uses of the novel stretchable therapeutic sleeves will now be set forth. They could be used after running to reduce or prevent swelling. They could be used after surgery and when a person's foot needs to be elevated. Other uses would be by diabetics and pregnant women with hot feet or swollen ankles. They could further be used when a person has edema, a sprained ankle, and broken bones. Additionally they could be used after any type of surgery that needs to have heat or cooling applied to a foot or body limb.

DESCRIPTION OF THE DRAWINGS

FIG. 1 is a front perspective view of the novel therapeutic sleeve for a human limb showing portions broken away for clarity;

FIG. 2 is a cross sectional view taken along lines 2—2 of FIG. 1;

FIG. 3 is a side elevation view illustrating the novel therapeutic sleeve worn on a person's leg;

FIG. 4 is a top plan view of an alternative embodiment of the therapeutic sleeve for a human limb;

FIG. 5 is a side elevation view showing the alternative embodiment worn on a person's foot with portions broken away for clarity;

FIG. 6 is a top plan view of the hot or cool foot pack utilized with the alternative embodiment illustrated in FIG. 5; and FIG. 7 is a front perspective view illustrating the alternative embodiment therapeutic sleeve partially installed on a person's foot.

DESCRIPTION OF THE PREFERRED EMBODIMENT

The novel therapeutic sleeve for human limbs will now be described by referring to FIGS. 1–7 of the drawings.

In FIGS. 1–3, the therapeutic sleeve is generally designated 10 and it has a primary tubular member 11. It has an upper elastic strip 12 and a lower elastic strip 13. A pocket wall 15 has a top edge 17 and side edges 18 and 19. A hot or cool pack 22 is removably received in the packet compartment 24.

A drawstring 26 passes through upper horizontal sleeve 27 and it has a barrel cord lock 28. Lower horizontal sleeve 30 has a drawstring 31 and it has a barrel cord lock 32.

Therapeutic sleeve 10 is shown mounted on person's leg 36 and above their foot 38. Primarily tubular member is preferably made of a stretchable material such as lycra and the pocket wall could be made of a cotton/nylon fabric.

An alternative embodiment therapeutic sleeve 40 is illustrated in FIG. 4–7. It has liner sleeve 42 having a top end 43 and a bottom edge 44. An upper elastic strip 46 is formed adjacent top end 43. Primary tubular member 48 has a top end 49 and a bottom edge 50. The respective bottom edges 44 and 50 are connected together by stitches 51 to form a end for each of these members.

Primary tubular member 48 has a foot portion 54 and a leg portion 56. A drawstring 58 is positioned intermediate these two portions.

The hot or cool foot pack 60 of FIG. 6 is shown positioned on a person's foot in FIGS. 5 and 7. The liner sleeve 42 is initially pulled onto the person's foot 38 and then the person puts his foot onto foot rest portion 62 of foot pack 60. The wings or flaps 63 and 64 are then folded over the top of the person's foot and the respective Velcro fastener members 66 and 68 are detachably secured together. Foot pack 60 has a front end 70 and a rear end 71. It also has side edges 72 and 73. A separate cool or hot pack 80 would be folded around the person's ankle prior to leg portion 56 being pulled up thereover. Traction gripping members 82 are on the bottom surface of foot pack 60.

What is claimed is:

1. A stretchable therapeutic sleeve comprising:

a liner sleeve of stretchable material for slipping over a foot; said liner sleeve having a top end, a bottom edge, an inner surface and an outer surface;

a primary tubular member of stretchable material for being inverted over said liner sleeve; said primary tubular member having a foot portion, a leg portion, an inner surface and an outer surface; said foot portion having a bottom edge;

means securing the bottom edges of said tubular member and said liner sleeve together;

a hot or cool foot pack having an elongated footrest portion; said footrest portion having a front end, a rear end, and laterally spaced left and right side edges; a left flap member extending laterally from said left edge adjacent its front end; a right flap member extending laterally from said right edge adjacent its front end; means for detachably securing said left flap member and said right flap member together after they have been folded across the top of a person's foot.

2. A stretchable therapeutic sleeve as recited in claim 1 further comprising traction gripping members on the outer surface of said foot portion of said primary tubular member.

3. A stretchable therapeutic sleeve as recited in claim 2 further comprising a drawstring positioned between the foot portion and the leg portion of said primary tubular member.

4. A stretchable therapeutic sleeve as recited in claim 1 further comprising a transversely extending drawstring positioned intermediate said foot portion and said leg portion of said primary tubular member.

* * * * *